(12) United States Patent
Rostamlou

(10) Patent No.: US 10,215,266 B2
(45) Date of Patent: Feb. 26, 2019

(54) GEARED CONTINUOULSLY VARIABLE TRANSMISSION

(71) Applicant: Alireza Rostamlou, Tehran (IR)

(72) Inventor: Alireza Rostamlou, Tehran (IR)

( * ) Notice: Subject to any disclaimer, the term of this patent is extended or adjusted under 35 U.S.C. 154(b) by 142 days.

(21) Appl. No.: 15/466,845

(22) Filed: Mar. 22, 2017

(65) Prior Publication Data

US 2017/0299034 A1 Oct. 19, 2017

Related U.S. Application Data

(63) Continuation of application No. PCT/IB2015/057273, filed on Sep. 21, 2015.

(30) Foreign Application Priority Data

Sep. 22, 2014 (IR) .................... 13935014000300697

(51) Int. Cl.
| | | |
|---|---|---|
| *F16H 47/04* | (2006.01) | |
| *A61L 27/04* | (2006.01) | |
| *A61L 27/06* | (2006.01) | |
| *A61L 27/30* | (2006.01) | |
| *A61L 31/02* | (2006.01) | |
| *A61L 31/08* | (2006.01) | |
| *A61L 33/02* | (2006.01) | |

(Continued)

(52) U.S. Cl.
CPC ............ *F16H 47/04* (2013.01); *A61L 27/047* (2013.01); *A61L 27/06* (2013.01); *A61L 27/306* (2013.01); *A61L 31/022* (2013.01); *A61L 31/088* (2013.01); *A61L 33/022* (2013.01); *A61L 33/027* (2013.01); *H02S 40/44* (2014.12); *A61L 2400/12* (2013.01); *A61L 2400/18* (2013.01); *A61L 2430/20* (2013.01); *F16H 2200/2007* (2013.01); *F24S 2020/17* (2018.05)

(58) Field of Classification Search
CPC .................................................. F16H 37/0846
See application file for complete search history.

(56) References Cited

U.S. PATENT DOCUMENTS

| 4,644,820 A * | 2/1987 | Macey ................ F16H 37/0846 |
| | | 475/211 |
| 4,824,419 A * | 4/1989 | Kumm ...................... F16H 9/10 |
| | | 474/49 |

(Continued)

*Primary Examiner* — Derek D Knight
(74) *Attorney, Agent, or Firm* — NovoTechIP International PLLC

(57) ABSTRACT

A geared continuously variable transmission (GCVT) is provided. The GCVT includes a first set of solar gears having a first solar gear and first plurality of connection components. Power enters the GCVT through the first set of solar gears. The GCVT includes a second set of solar gears having a second solar gear and second plurality of connection components. Power exits the GCVT through the second set of solar gears. Power is transmitted from the first set of solar gears to the second set of solar gears via the first plurality of connection components and the second plurality of connection components. The GCVT includes a hydraulic pump and a hydraulic motor connecting first component from the first plurality of connection components to second component from the second plurality of connection components and providing constant rotation ratio between the first component and the second component.

12 Claims, 10 Drawing Sheets

(51) Int. Cl.
*H02S 40/44* (2014.01)
*F24S 20/00* (2018.01)

(56) References Cited

U.S. PATENT DOCUMENTS

2014/0274539 A1* 9/2014 Orton .................. F16H 3/74
  475/205
2014/0349800 A1* 11/2014 Correa Cely ........... F16H 3/724
  475/149

* cited by examiner

GEARED CONTINUOUSLY VARIABLE TRANSMISSION

CROSS REFERENCE TO RELATED APPLICATION

This application claims the benefit of priority to Iran patent application serial number 139350140003006972 filed on Sep. 22, 2014, which subsequently issued as Iran patent number 85650 on May 13, 2015, and to PCT/IB32015/057273 filed on Sep. 21, 2015, all of which are incorporated by reference herein in their entireties.

TECHNICAL FIELD

The present application relates generally to transmissions and, more particularly, to a geared continuously variable transmission (GCVT) for producing high torque output, high power transmission and efficiency of the transmission.

BACKGROUND

Transmissions are used in transportation, agricultural and construction equipment to transmit power from power sources, such as internal combustion engines to equipment for accomplishing a desired task. For example, transmissions are used to properly transmit power to the wheels of a vehicle, or to a vehicle implement. Various industries use gear mechanisms for transmission and conversion of engine power. Various gearbox types such as, for example, gearboxes with constant or variable transmission rates are used. Gearboxes have multiple advantages such as capability of transmission of high torques, low depreciation rate, constant transmission for a selected rotation rate, and high efficiency. However, despite of multiple advantages, the gearboxes have disadvantages such as, for example, limited number of transmission rates, and stepwise (non-linear) transmission rates, which can lower efficiency and cause difficulty in selection of a suitable torque.

Continuously variable transmission (CVT) can be used to overcome the above mentioned disadvantages of gearboxes. A continuously variable transmission (CVT) is a transmission that can change through an infinite number of effective gear ratios between a minimum and a maximum range. In contrast, non-CVT transmissions offer a fixed number of gear ratios. Specifically, hydrostatic CVTs may use a variable displacement pump and a hydraulic motor and transmit power using hydraulic fluid. A swash plate may be used within the variable displacement pump to vary the output of the hydrostatic CVT by adjusting the fluid flowing into the hydraulic motor. Thus, the swash plate may enable the hydrostatic CVT to be continuously variable. Some hydrostatic CVTs may be combined with gear assemblies, drive shafts, and clutches to create a hydro-mechanical CVT. It may be appreciated that in certain applications, such as in construction equipment, a high torque output may be utilized by implements of the construction equipment. Further, a high torque output may be beneficial for low speed movement of vehicles, such as construction vehicles or agricultural vehicles.

In CVTs, transmission rate between an input shaft and an output shaft can be changed continuously in a linear manner such that infinite number of transmission rates is available between predefined lower and upper limits. In a CVT, transmission is provided by friction between parts of the CVT. For example, in a belt driven CVT, friction between a belt and a pulley and in a toroidal CVT, friction between a toroid and disks of the CVT cause the transmission.

However, using the friction mechanism in CVTs cause problems such as limited transmission capability, high depreciation, low efficiency, and lack of stability in the selected revolution. Hence there is a need for a GCVT to produce efficient transmission with continuous/linear variation and high torque output and high power transmission

SUMMARY

The disclosed subject matter relates to a geared continuously variable transmission (GCVT). The GCVT includes a first set of solar gears having a first solar gear and a first plurality of connection components. Power enters the GCVT through the first set of solar gears. The GCVT includes a second set of solar gears having a second solar gear and a second plurality of connection components. Power exits the GCVT through the second set of solar gears. Power is transmitted from the first set of solar gears to the second set of solar gears via the first plurality of connection components and the second plurality of connection components. The GCVT includes a hydraulic pump and a hydraulic motor connecting a first component from the first plurality of connection components to a second component from the second plurality of connection components and providing constant rotation ratio between the first component and the second component. The hydraulic pump and the hydraulic motor can be connected to each other via a hydraulic pipe.

Each of the first plurality of connection components and the second plurality of connection components may include a shaft fixed to the respective solar gear, one or more pinion gears, a carrier, and a ring gear. The power transmission from the first set of solar gears to the second set of solar gears can be performed by a geared interface shaft. In some instances, the power transmission from the first set of solar gears to the second set of solar gears can be performed by an interface gear. In some other instances, the power transmission from the first set of solar gears to the second set of solar gears can be performed by direct geared connection between one of the first plurality of connection components to a counterpart component from the second plurality of connection components.

The power transmission from the first set of solar gears to the second set of solar gears can be performed by direct solid connection between one of the first plurality of connection components to a counterpart component from the second plurality of connection components. In some instances, the power transmission from the first set of solar gears to the second set of solar gears can be performed by direct coupling of the hydraulic motor and the hydraulic pump with one of the first plurality of connection components and a counterpart component from the second plurality of connection components.

In some instances, the power transmission from the first set of solar gears to the second set of solar gears can be performed by direct coupling of each component form the first plurality of connection components to a counterpart component from the second plurality of connection components.

The GCVT may further include one or more sensors. The one or more sensors may monitor volume capacity of the hydraulic pump and the hydraulic motor. Moreover, an infinite number of transmission rates can be provided by the GCVT between a predefined lower limit number and a predefined upper limit number. A change in the transmission rates can be continuous in a linear manner. In addition, at least one of the hydraulic pump and the hydraulic motor may have a variable volume flow rate.

The hydraulic pump may be configured to connect to the first plurality of connection components and the second plurality of connection components via a first geared interface shaft component. The first geared interface shaft component may include a first geared interface shaft, a first gear connected to the first geared interface shaft and a first component from the first plurality of connection components, a second gear connected to the first geared interface shaft and a second component from the second plurality of connection components, and a third gear connected to the first geared interface shaft and a gear of the hydraulic pump.

The hydraulic motor may be configured to connect to the first plurality of connection components and the second plurality of connection components via a second geared interface shaft component. The second geared interface shaft component may include a second geared interface shaft, a first gear connected to the second geared interface shaft and a third component from the first plurality of connection components, a second gear connected to the second geared interface shaft and a fourth component from the second plurality of connection components, and a third gear connected to the first geared interface shaft and a gear of the hydraulic motor.

BRIEF DESCRIPTION OF THE DRAWINGS

Features of the subject technology are set forth in the appended claims. However, for purpose of explanation, several implementations of the subject technology are set forth in the following figures.

DETAILED DESCRIPTION

Figure 1:
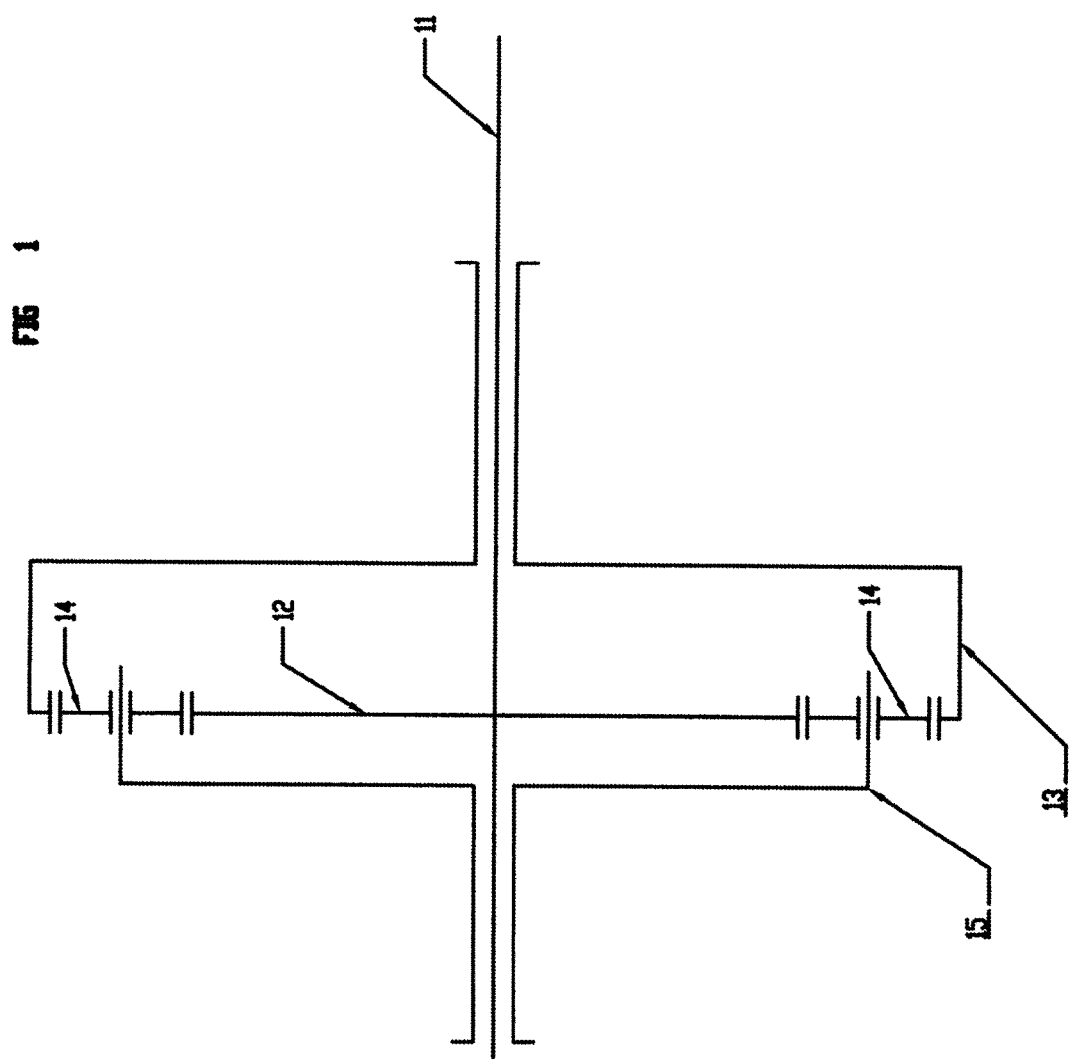
FIGS. 1-10 illustrate components of an exemplary Geared Continuously Variable Transmission (GCVT).

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

A Geared Continuously Variable Transmission (GCVT) is a geared transmission system that benefits from the advantages of gearboxes while solving the disadvantage of stepwise (non-linear) transmission of gearboxes. A GCVT, as disclosed, may include a shell, two sets of solar gears, two sets of connection components and a hydraulic pump and a hydraulic motor. In some instances, at least one of the hydraulic pump and the hydraulic motor may have variable volume capacity ($V_g$). The GCVT may also include safety hydraulic components.

A first set of solar gears, from the two sets of solar gears, can be used for inputting power to the GCVT. The power can enter the GCVT via one of the components of the first set of solar gears (e.g., input component) such as, for example, a shaft (e.g., a shaft connected to a solar gear), a ring gear, a carrier (e.g., planetary carrier), etc. A second set of solar gears, from the two sets of solar gears, can be used for outputting the power from the GCVT. The power can exit the GCVT via one of the components of the second set of solar gears (e.g., output component) such as, for example, a shaft (e.g., a shaft connected to a solar gear), a ring gear, a carrier (e.g., a planetary carrier), etc. Power transmission by the GCVT is performed by connection among components of the two sets of solar gears (excluding the input and output components). The components of the two sets of solar gears can be connected to each other by various methods such as, for example, an interface shaft between the gears, an interface gear, direct connection of the components using gears, solid connection of the components, etc.

For example, when the components of the two sets of solar gears are connected via interface shafts, the connection can be described as follows. A first shaft having connecting gears can connect a first component from the first set of solar gears to a first component from the second set of solar gears such that a constant rotation is maintained between the two components. A second shaft having connecting gears can connect a second component from the first set of solar gears to a second component from the second set of solar gears such that a constant rotation is maintained between the two components. The hydraulic pump and motor can be connected to the first and second shafts respectively using interface gears. A hydraulic pipe can connect an output of the hydraulic pump to an input of the hydraulic motor. In this case, a constant rotation is generated between the hydraulic pump and the hydraulic motor and as a result between the first and the second shafts.

The GCVT as described can function with a constant transmission rate. By changing the volume capacity of the hydraulic pump and/or hydraulic motor, the rotation ratio of their axes and the rotation ratio of the two interface shafts can change. By changing the rotation ratio of the two interface shafts which carry torque between the components of the two sets of solar gears, the transmission rate of the gearbox can change. Since the change in volume capacity ($V_g$) of a hydraulic pump and/or hydraulic motor is continuous, the change in transmission rate of the GCVT is also continuous.

An example connection between the components of the two sets of solar gears is described herein in more detail. Among the main components of the first set of solar gears such as, shaft, ring gear and carrier, the shaft (e.g., first shaft) can be considered as the main input component of power. Similarly, the second shaft from the second set of solar gears can be considered as the output component. In addition, two counterpart components from the two sets are considered to be connected to each other by an interface shaft. For example, the first ring gear from the first set is a counterpart of the second ring gear from the second set and the first carrier from the first set is a counterpart of the second carrier from the second set. A gear can be installed on each of the first and second ring gears and first and second carriers. Interface shafts are used to connect counterpart components from the two sets.

The first interface shaft may have three fixed gears. A first fixed gear of the first interface shaft can be connected to a gear installed on the first ring gear from the first set. The second fixed gear of the first interface shaft can be connected to a gear installed on the second ring gear from the second set. As a result, the first interface shaft connects the first ring gear from the first set with its counterpart second ring gear from the second set and maintains a constant rotation ratio among the two. Similarly, the second interface shaft may have three fixed gears. A first fixed gear of the second interface shaft can be connected to a gear installed on the first carrier from the first set. The second fixed gear of the second interface shaft can be connected to a gear installed on the second carrier from the second set. As a result, the second interface shaft connects the first carrier from the first set with its counterpart second carrier from the second set and maintains a constant rotation ratio among the two.

In addition, a gear can be installed on the axis of the hydraulic pump and another gear can be installed on the axis of the hydraulic motor. In this case, the third gear of the first interface shaft can be connected with the gear of the hydraulic pump and the third gear of the second interface shaft can be connected with the gear of the hydraulic motor, such that a constant rotation (K) can be created between rotation of the two axes of the hydraulic pump and the hydraulic motor. Moreover, a constant ratio (H) can be created between rotation of the first interface shaft and the second interface shaft, which are connected to the gears of the hydraulic pump and the hydraulic motor. The ratio H is a function of ratio K.

The structure of the GCVT can be completed by using a hydraulic valve, a hydraulic relief valve and a hydraulic damper. The GCVT as described, can work with a constant transmission rate. As shown in equations of Table 1 when the ratio H between rotation of the first interface shaft and the second interface shaft is changed, the transmission rate of the GCVT may also change. As previously noted, at least one of the hydraulic pump and hydraulic motor may have variable volume capacity ($V_g$). In this case, by changing the volume capacity, the ratio K between the axes of the hydraulic pump and the hydraulic motor can change. As a result ratio H, a function of K, may also change and this can cause the transmission rate of the GCVT to change.

In Table 1, N is the rotation speed of a gear or shaft, G is a number of teeth of a gear, $V_g$ is the volume capacity of the hydraulic pump and motor, and Q is volume flow rate of the hydraulic pump and motor. An index shows the component number. For example $G_{12}$ is the number of teeth of gear 12 and $N_{12}$ is the rotation speed of gear 12.

TABLE 1

$N_{12}*G_{12} + N_{13}*G_{13} = N_{15}*(G_{12} + G_{13})$
$N_{22}*G_{22} + N_{23}*G_{23} = N_{25}*(G_{22} + G_{23})$
$N_2 = N_{13}*G_{16}/G_{19} = N_{23}*G_{26}/G_{29}$
$N_3 = N_{15}*G_{17}/G_{18} = N_{25}*G_{27}/G_{28}$
$Q_7 = Q_8$
$Q_7 = N_2*G_{20}*V_{g7}/G_6$
$Q_8 = N_3*G_4*V_{g8}/G_5$
$N_2/N_3 = G_4*G_6*V_{g8}/(G_5*G_{20}*V_{g7})$
$K = V_{g8}/V_{g7}$
$H = N_2/N_3$
$H = K*G_4*G_6/(G_5*G_{20})$

Since in hydraulic systems variations of volume capacity are continuous, therefore variations in K and H and the transmission rate of the GCVT are continuous as well. The tests and studies show that in the GCVT as described, majority of the power (e.g., torque and angular speed) may be transferred by the two interface shafts, which connect the counterpart components, as previously discussed, and a small part of the power is transferred via the hydraulic pump and hydraulic motor. As a result, the GCVT has advantages such as capability of transferring high and low powers, low depreciation, high efficiency, constant transmission rate based on selection, and low cost.

Figure 2:
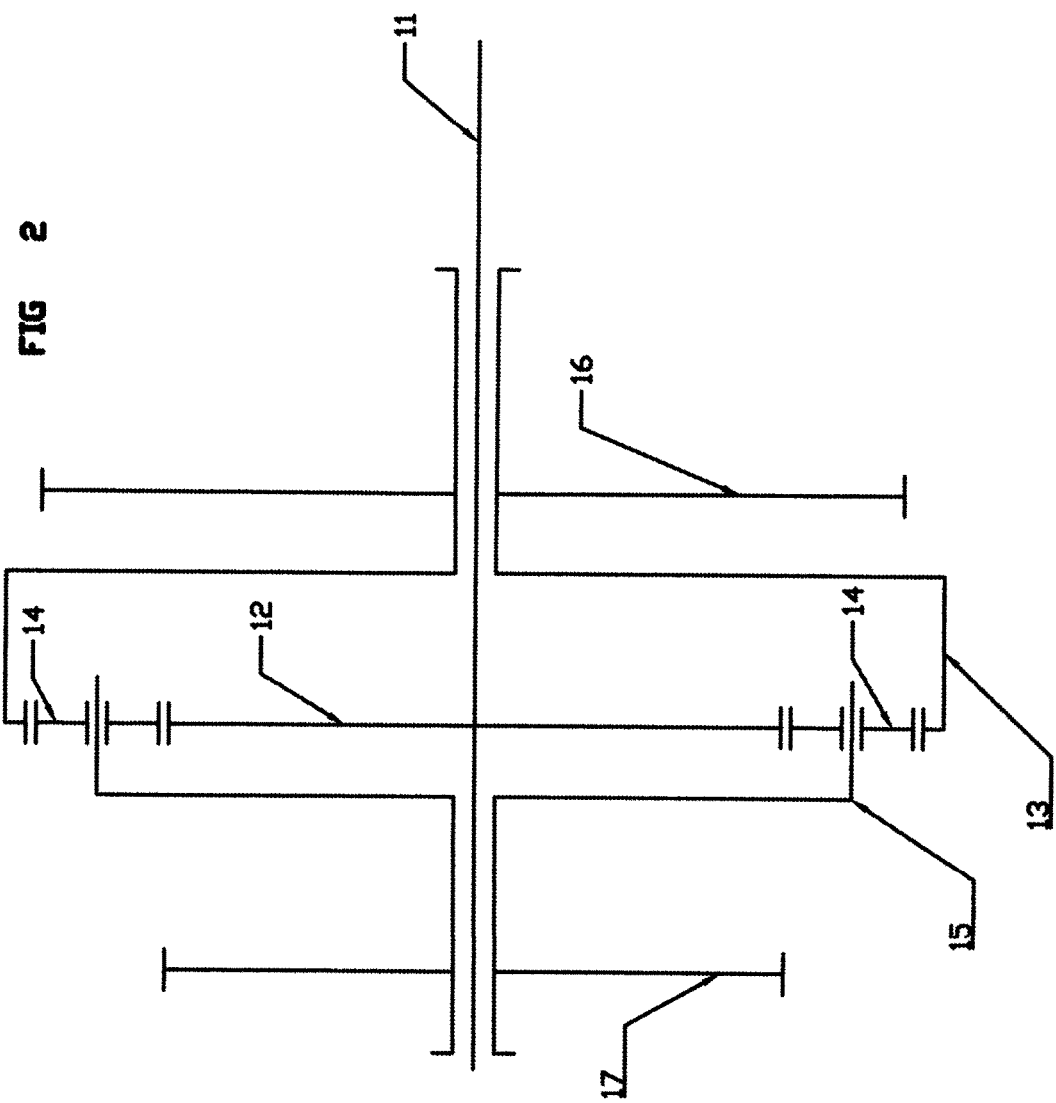

FIG. 1 illustrates the first set of solar gears. As shown in FIG. 1, the shaft 11 is installed onto the solar gear 12 and the two components may produce an integrated component. One or more pinions 14 can be attached to carrier 15. In the illustration of FIG. 1 two pinons 14 are shown. The carrier 15 is installed on shaft 11 and can freely rotate around the shaft's axis. A ring gear 13 is installed on shaft 11 and can freely rotate around the shaft's axis In FIG. 2, two gears 16 and 17 are installed on the first set of solar gears such that gear 16 is installed on ring gear 13 and the two components can produce an integrated component. The gear 17 is installed on carrier 15 and the two components can produce an integrated component.

Figure 3:
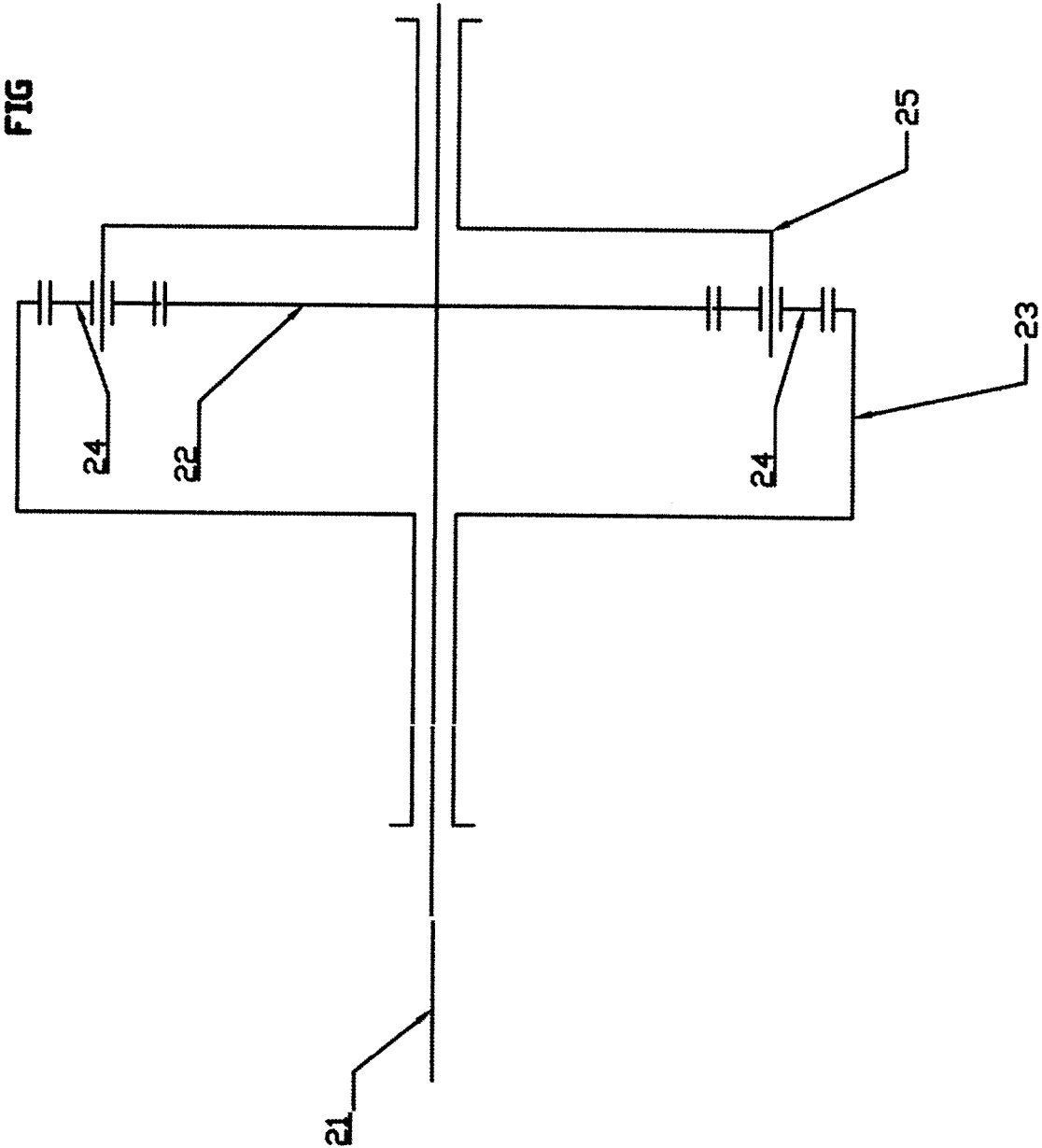

FIG. 3 illustrates the second set of solar gears. As shown in FIG. 3, the shaft 21 is installed onto the solar gear 22 and the two components may produce an integrated component. One or more pinions 24 can be attached to carrier 25. The carrier 25 is installed on shaft 21 and can freely rotate around the shaft's axis. A ring gear 23 is installed on shaft 21 and can freely rotate around the shaft's axis.

Figure 4:
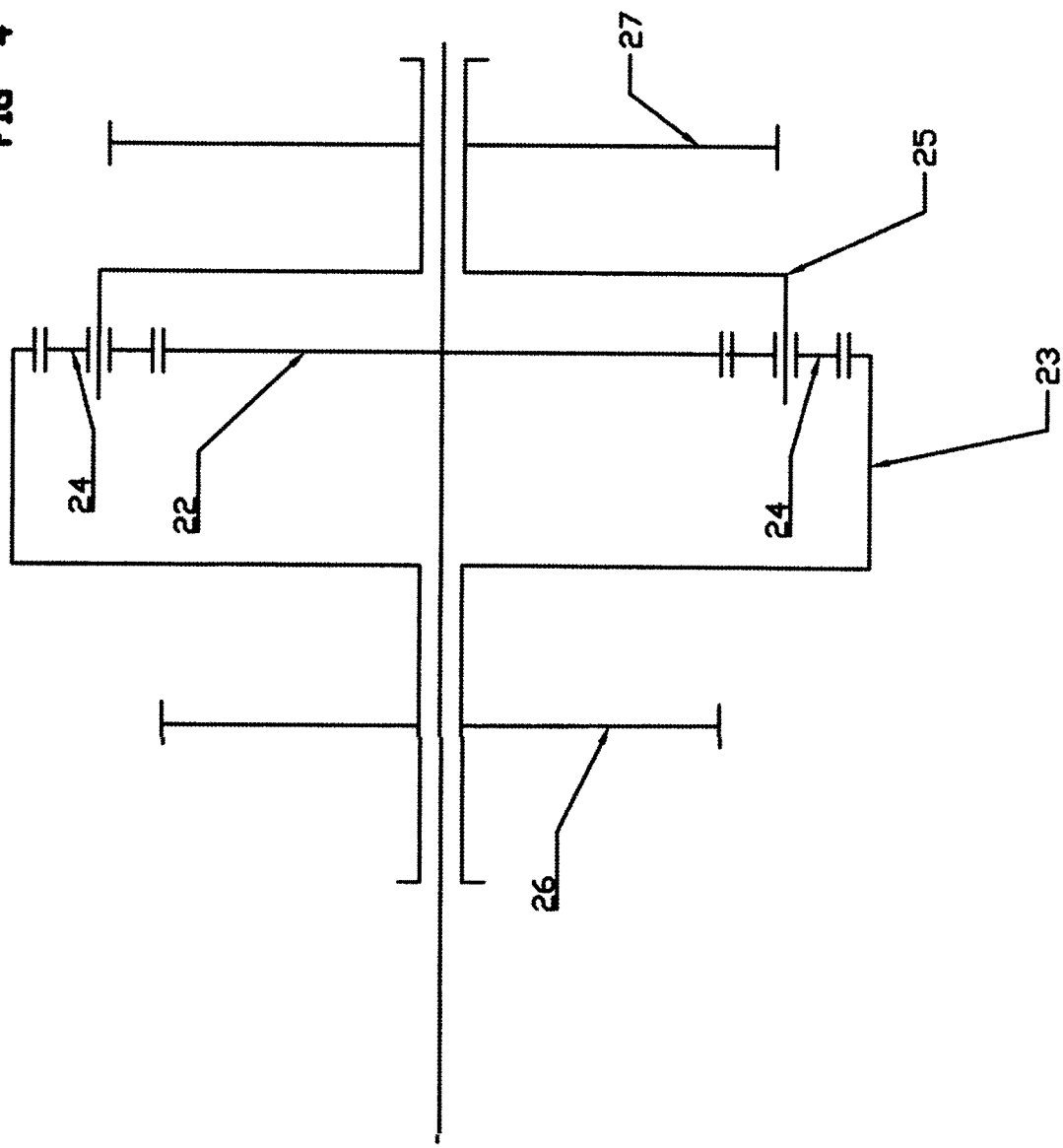

In FIG. 4, two gears 26 and 27 are installed on the second set of solar gears such that gear 26 is installed on ring gear 23 and the two components can produce an integrated component. The gear 27 is installed on carrier 25 and the two components can produce an integrated component.

Figure 5:
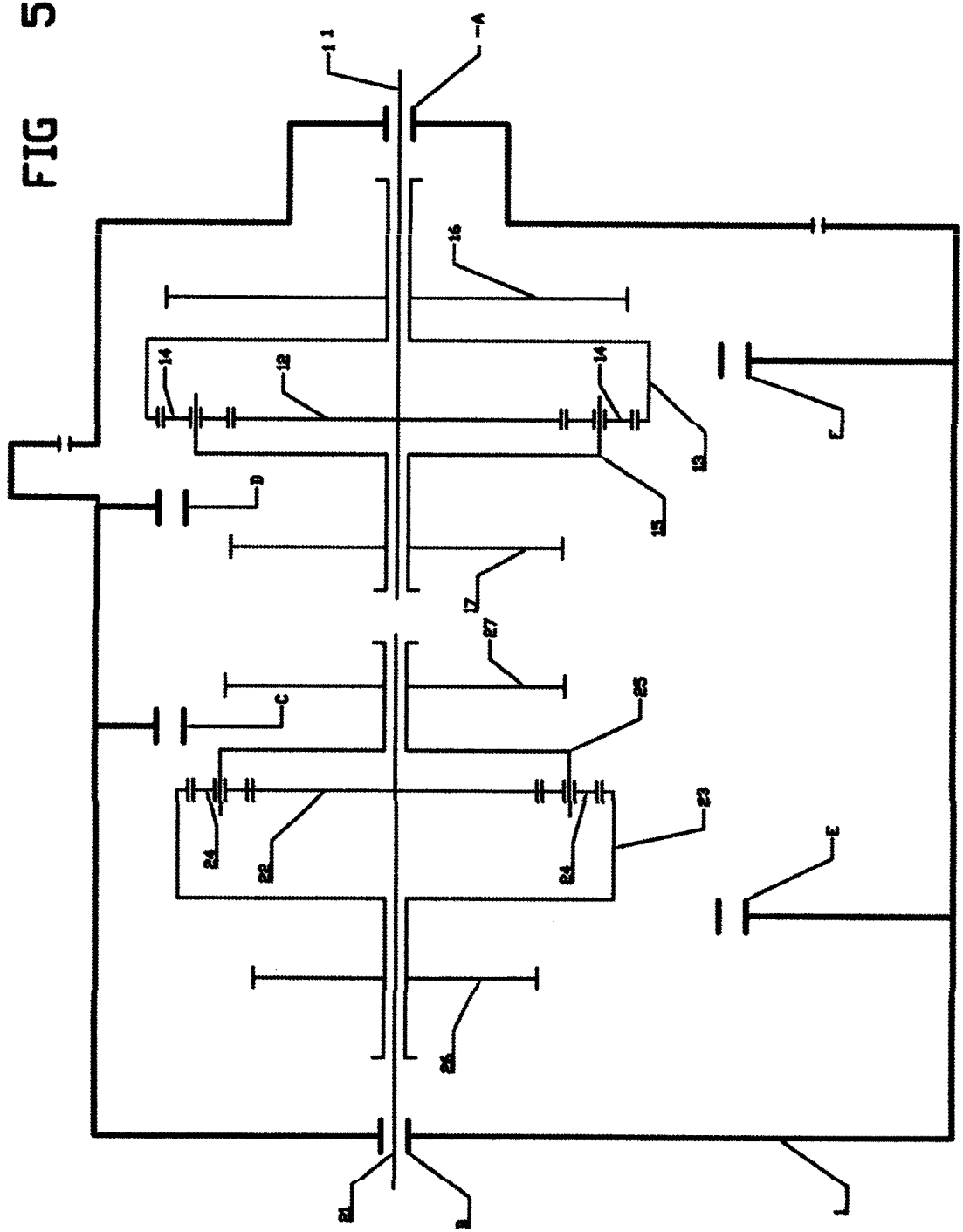

FIG. 5 illustrates the two sets of solar gears of FIGS. 1 and 3. As shown in FIG. 5, the first and the second set of solar gears are placed together such that the two sets facing each other on bearings A and B. In the combined structure of FIG. 5, the shaft 11 can be considered as input shaft of power (torque and rotation) and shaft 21 is the output shaft of power. For transferring the torque and rotation from the first set of solar gears to the second set of solar gears two shafts can be used with each shaft having three gears, as shown in FIG. 6.

Figure 6:
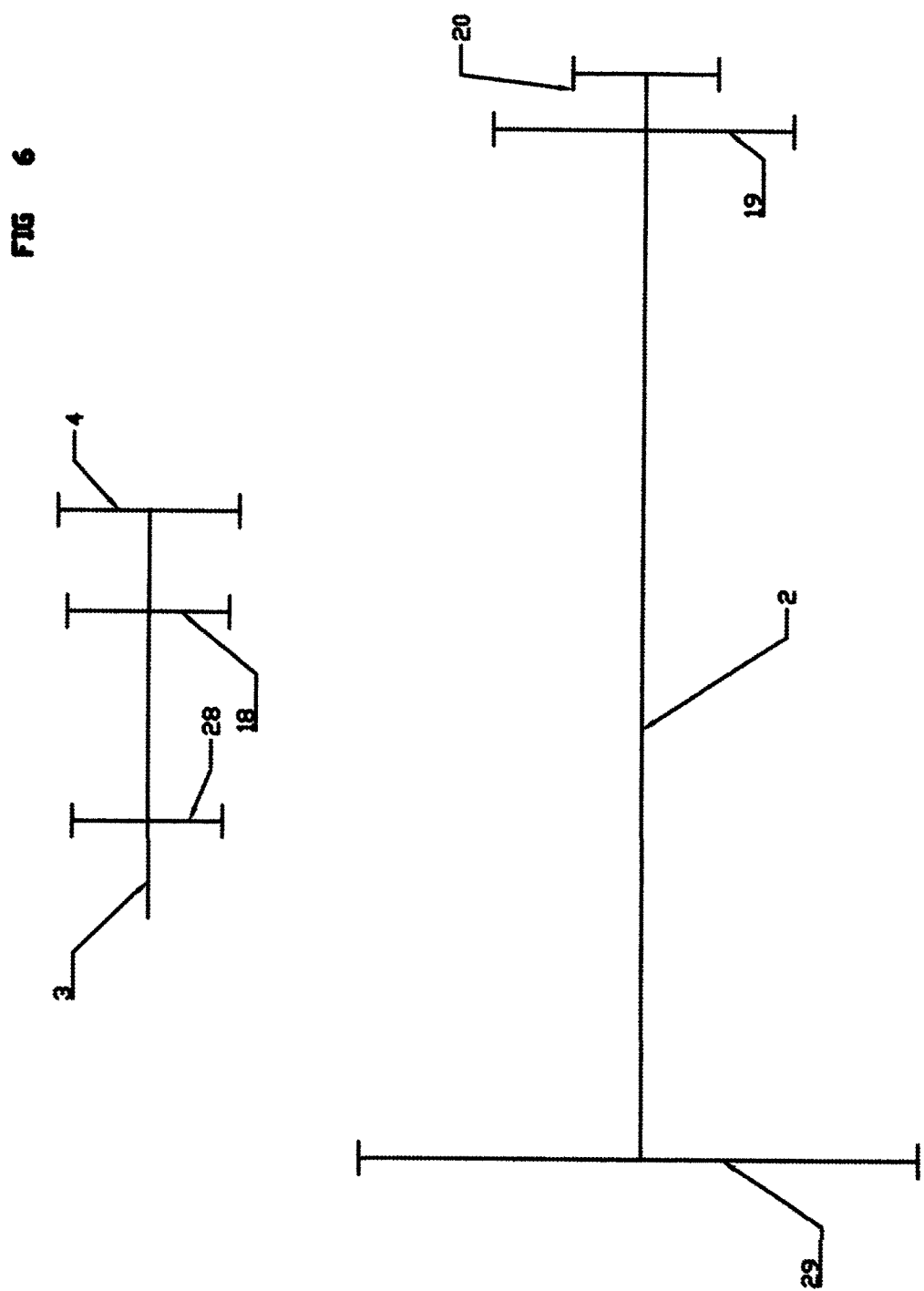

As shown in FIG. 6, the gears 19, 20 and 29 are installed on shaft 2. The shaft 2 and the gears 19, 20 and 29 can produce an integrated component. Similarly, gears 4, 18 and 28 are installed on shaft 3 and components 3, 4, 18 and 28 can produce an integrated component.

Figure 7:
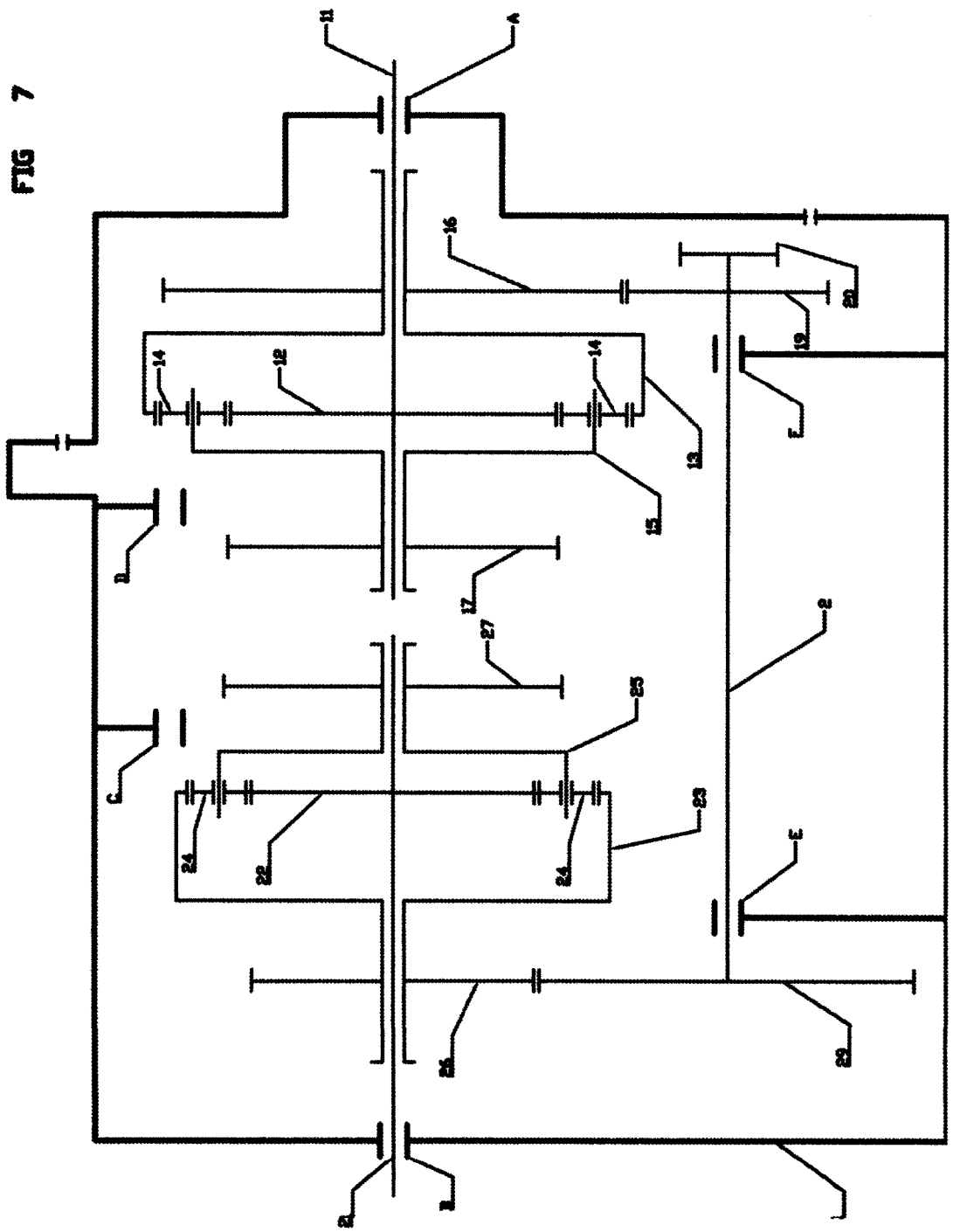

FIG. 7 illustrates shaft 2 as shown in FIG. 6. The shaft 2 can be placed on two bearings E and F. The gear 19 of shaft 2 is engaged with gear 16 and the gear 29 of shaft 2 is engaged with gear 26. In this case, shaft 2 can transfer torque and rotation from ring gear 13 (of the first set of solar gears) to ring gear 23 (from the second set of solar gears). The shaft 2 can generate a stable ratio revolution between the two ring gears 13 and 23.

Figure 8:
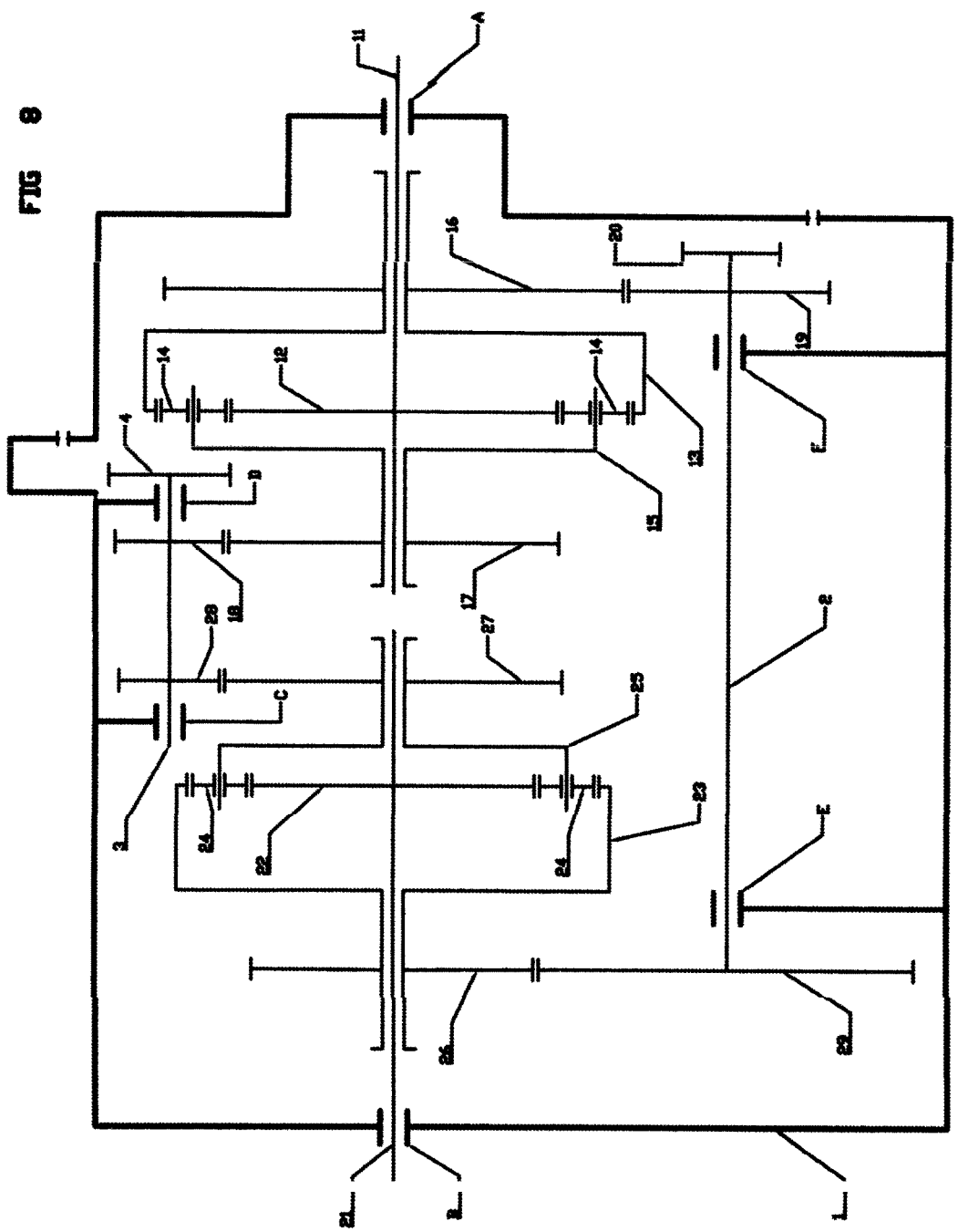

FIG. 8 illustrates shaft 3 as shown in FIG. 6. The shaft 3 can be placed on two bearings C and D. The gear 18 of shaft 3 is engaged with gear 17 and the gear 28 of shaft 3 is engaged with gear 27. In this case, shaft 3 can transfer torque and rotation from carrier 15 (of the first set of solar gears) to carrier 25 (from the second set of solar gears). The shaft 3 can generate a stable ratio revolution between the two carriers 15 and 25.

As shown in FIG. 5, each of the first and second sets of solar gears can have two degrees of freedom. As shown in FIGS. 7 and 8, the shafts 2 and 3 provide two connections between components of the two sets of solar gears and balance the two degrees of freedom. In order to achieve one degree of freedom for the GCVT structure, the shafts 2 and 3 can be connected by a hydraulic system as shown in FIG. 9.

Figure 9:
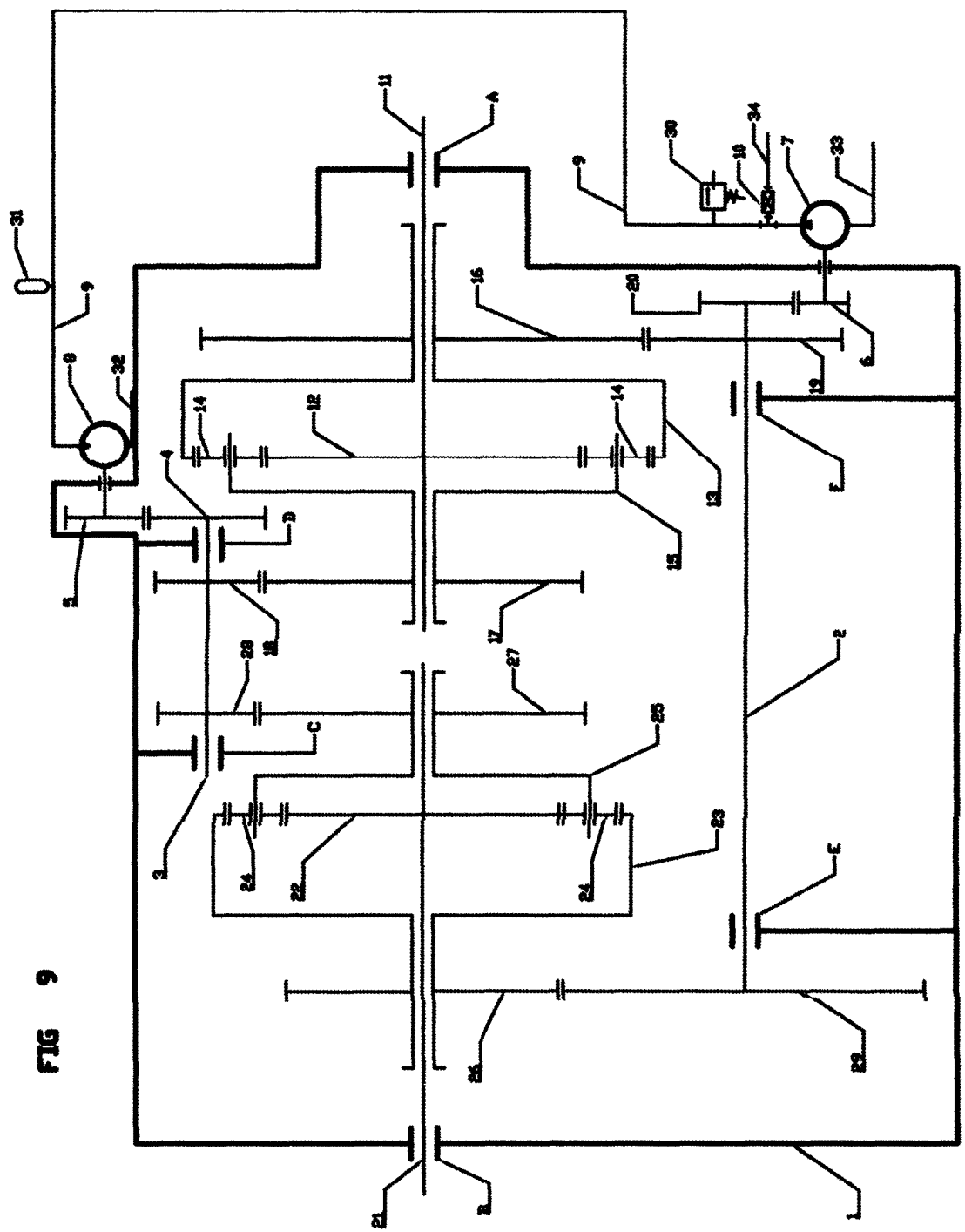

FIG. 9 illustrates a hydraulic pump 7 and a gear 6 installed on a shaft of the hydraulic pump 7. The gear 6 is engaged with gear 20 (installed on shaft 2). Furthermore, a gear 5 is installed on a shaft of the hydraulic motor 8. The gear 5 is engaged with gear 4 (installed on shaft 3). A hydraulic pipe 9 connects an output fluid canal of the hydraulic pump 7 to an input fluid canal of the hydraulic motor 8. The three hydraulic pipes 33 (input to the hydraulic pump 7), 32 (output of the hydraulic motor 8), and 34 (output of the hydraulic valve 10) are connected to a hydraulic oil tank (not shown). Component 31 is a hydraulic damper and component 30 is a hydraulic relief valve. Component 10 is a hydraulic valve for hydraulic connection and disconnection. Connection between the oil output from the hydraulic pump 7 to the input of the hydraulic motor 8 can create an equivalent volume flow rate for the pump and the motor. In this case, the gears 5 and 6 can rotate with a constant ratio and as a result the two shafts 2 and 3 can also have a constant rotation ratio. This may create one degree of freedom for the GCVT mechanism. In this case, the GCVT mechanism has one degree of freedom.

As discussed with regards to FIG. 9, the GCVT mechanism can function with a constant rotation ratio (R). In this case, if the volume flow rate of the hydraulic pump 7 or the hydraulic motor 8 is changed, this change can cause the ratio of rotation speed of shaft 2 to rotation speed of shaft 3 to change. This in return can cause a change in the conversion rate (rotation ratio) R such that a ratio of the rotation of output shaft 21 to the rotation of the input shaft 11 may also change.

An example discussed below shows the continuity of the changes. As previously described with respect to Table 1, in the following equations N is the rotation speed of a gear or shaft, G is a number of teeth of a gear, $V_g$ is the volume capacity of the hydraulic pump and motor, and Q is the volume flow rate of the hydraulic pump and hydraulic motor. An index shows the component number. For example $G_{12}$ is the number of teeth of gear 12 and $N_{12}$ is the rotation speed of gear 12.

When the hydraulic valve 10 is open (in this case, the pipe 9 is connected to the hydraulic oil tank via hydraulic pipe 34), the hydraulic pump is disconnected from the hydraulic motor and therefore shafts 2 and 3 are disconnected. In this case the GCVT mechanism may reach the two degrees of freedom or the GCVT may be in neutral state (the mechanism becomes idle).

In some instances, sensors can be installed in the power consuming set or in the power producing set such that the volume capacity of the hydraulic pump 7 and motor 8 can be automatically controlled using the sensors.

In some instances, some of the gears and interface shafts can be omitted such that the counterpart components connect directly to each other. For example, the hydraulic pump 7 and motor 8 can be directly coupled with their counterpart shafts and the gears connecting the hydraulic pump 7 and the hydraulic motor 8 can be omitted.

In some other instances, the rotation speed of the counterpart components from the two sets of solar gears can be preset to be equal. In such cases, there may be no need for interface shafts and interface gears between the counterpart components, because the two counterpart components can be coupled to each other.

Figure 10:
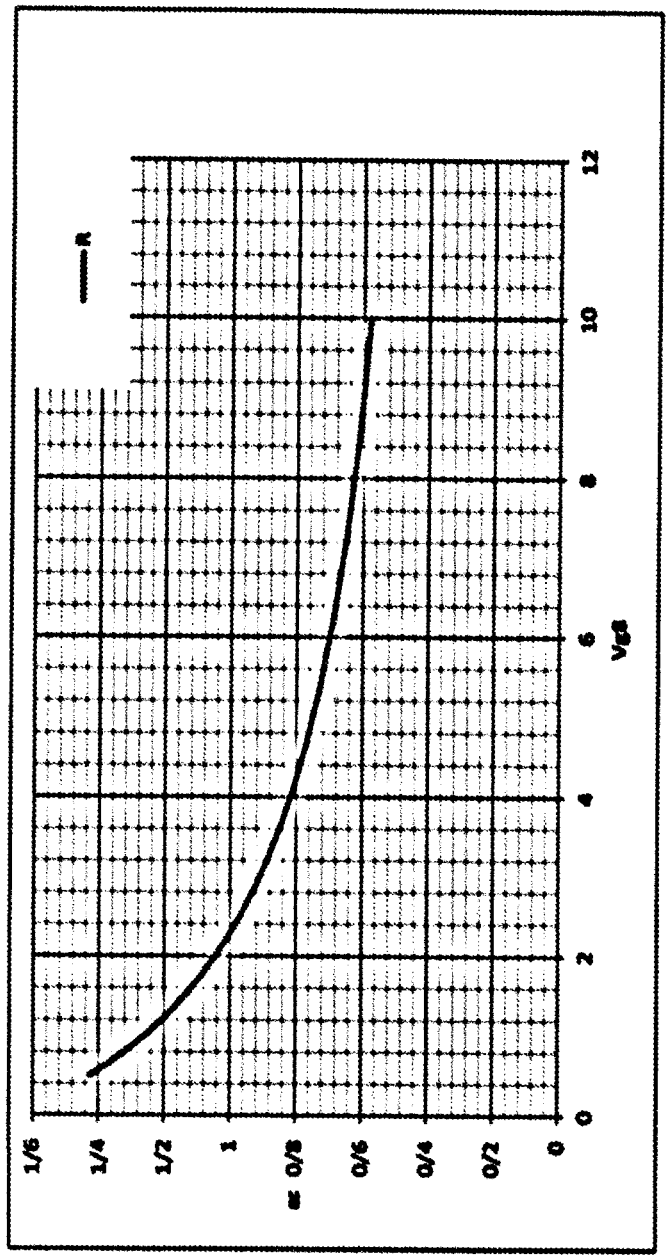

FIG. 10 is graph representation of the conversion rate R as calculated below. The equations that follow are used to calculate a ratio of rotational speed of the output shaft of the GCVT (shaft 21 coupled to gear $G_{22}$ in FIG. 9) to the rotation speed of the input shaft of the GCVT (shaft 11 coupled to gear $G_{12}$ in FIG. 9). This ratio represents the conversion rate R of the GCVT.

Equations 1-4 calculate the rotational speed of the solar gears. Equation 5 is a combination of equations 3 and 4, and equation 7 is resulted when equation 6 is assumed. Equation 10 is a combination of equations 8 and 9, and equation 12 is resulted when equation 11 is assumed.

Considering that the output of hydraulic pump 7 is connected to the input of the hydraulic motor 8, the volume flow rate of the pump 7 and motor 8 may be equal ($Q_7=Q_8$). Following the relation between the volume flow rate, rotational speed and the volume capacity equation 15 is resulted, wherein $V_g$ represents the volume capacity of the hydraulic set in each rotation of its shaft in cubic centimeters per rotation. Equation 16 is resulted from replacing value $N_6$ from equation 13 into equation 15 and equation 18 is resulted from replacing value $N_5$ from equation 14 into equation 17.

Equation 19 is resulted from a combination of equations 16 and 18, and equation 20 is resulted from replacing value N2 from equation 8 and value N3 from equation 3 into equation 19. And equation 22 is resulted from equation 21. With equation 22 as an assumption, equation 23 is resulted and equation 24 is resulted from a combination of equations 1 and 23.

Equation 25 is resulted from equation 2 and equation 26 is a combination of equations 7 and 23. Equation 27 is resulted from replacement of N25 from equation 26 and N23 from equation 12 into equation 25. Equation 28 is resulted from replacement of N13 from equation 24 into equation 27.

$$N_{12} \times G_{12} + N_{13} \times G_{13} = N_{15} \times (G_{12} + G_{13}) \quad 1)$$

$$N_{22} \times G_{22} + N_{23} \times G_{23} = N_{25} \times (G_{22} + G_{23}) \quad 2)$$

$$N_3 = -N_{15} \times G_{17}/G_{18} \quad 3)$$

$$N_3 = -N_{25} \times G_{27}/G_{26} \quad 4)$$

$$N_{25} = N_{15} \times G_{17} \times G_{28}/(G_{27} \times G_{18}) \quad 5)$$

$$A = G_{17} \times G_{28}/(G_{27} \times G_{18}) \quad 6)$$

$$N_{25} = A \times N_{15} \quad 7)$$

$$N_2 = -N_{13} \times G_{16}/G_{19} \quad 8)$$

$$N_2 = -N_{23} \times G_{26}/G_{29} \quad 9)$$

$$N_{23} = N_{13} \times G_{16} \times G_{29}/(G_{19} \times G_{26}) \quad 10)$$

$$B = G_{16} \times G_{29}/(G_{19} \times G_{26}) \quad 11)$$

$$N_{23} = B \times N_{13} \quad 12)$$

$$N_6 = -N_2 \times G_{20}/G_6 \quad 13)$$

$$N_5 = -N_3 \times G_4/G_5 \quad 14)$$

$$Q_7 = N_6 \times V_{g7} \quad 15)$$

$$Q_7 = -N_2 \times G_{20} \times V_{g7}/G_6 \quad 16)$$

$$Q_8 = N_5 \times V_{g8} \quad 17)$$

$$Q_8 = -N_3 \times G_4 \times V_{g8}/G_5 \quad 18)$$

$$N_2 \times G_{20} \times V_{g7}/G_6 = -N_3 \times G_4 \times V_{g8}/G_5 \quad 19)$$

$$N_{13} \times G_{16} \times G_{20} \times V_{g7}/(G_{19} \times G_6) = -N_{15} \times G_{17} \times G_4 \times V_{g8}/(G_{18} \times G_5) \quad 20)$$

$$N_{15} = -N_{13} \times G_{16} \times G_{20} \times G_{18} \times G_5 \times V_{g7}/(G_{19} \times G_6 \times G_{17} \times G_4 \times V_{g8}) \quad 21)$$

$$X = G_{16} \times G_{20} \times G_{18} \times G_5 \times V_{g7}/(G_{19} \times G_6 \times G_{17} \times G_4 \times V_{g6}) \quad 22)$$

$$N_{15} = -X \times N_{13} \quad 23)$$

$$N_{13} = -B_{12} \times G_{12}/(X \times (G_{12} + G_{13}) + G_{13}) \quad 24)$$

$$N_{22} = (N_{25} \times (G_{22} + G_{23}) - N_{23} \times G_{23})/G_{22} \quad 25)$$

$$N_{25} = -A \times X \times N_{13} \quad 26)$$

$$N_{22} = -(A \times X \times N_{13} \times (G_{22}+G_{23}) + B \times N_{13} \times G_{23})/G_{22} \quad 27)$$

$$N_{22} = N_{12} \times (A \times X \times G_{12} \times (G_{22}+G_{23}) + B \times G_{23} \times G_{12})/(X \times G_{22} \times (G_{12}+G_{13}) + G_{22} \times G_{13}) \quad 28)$$

$$R = N_{22}/N_{12} \quad 29)$$

$$R = (A \times G_{12} \times (G_{22}+G_{23}) \times X + B \times G_{23} \times G_{12})/(G_{22} \times (G_{12}+G_{13}) \times X + G_{22} \times G_{13}) \quad 30)$$

$$M = G_{18} \times G_{20} \times G_{18} \times G_5 \times V_{g7}/(G_{19} \times G_6 \times G_{17} \times G_4) \quad 31)$$

$$L = A \times G_{12} \times (G_{22}+G_{23}) \quad 32)$$

$$F = B \times G_{23} \times G_{12} \quad 33)$$

$$P = G_{22} \times (G_{12}+G_{13}) \quad 34)$$

$$C = G_{22} \times G_{13} \quad 35)$$

$$X = M/V_{g6} \quad 36)$$

$$R = (L \times M + F \times V_{g6})/(P \times M + C \times V_{g8}) \; R = f(V_{g8}) \quad 37)$$

Equation 29 represents the conversion rate of the GCVT. Equation 30 is resulted from replacement of N22 from equation 28 into equation 29. As previously discussed, one or both of the hydraulic pump 7 and hydraulic motor 8 may have variable volume flow rate, for example, the volume capacity of the hydraulic motor 8 can be variable. For simplification of the equations, assumptions 31 to 35 are made. Equation 36 is resulted from a combination of equations 31 and 22 and equation 37 is resulted from a combination of equations 32 to 36 into equation 30. The parameters L, M, F, P, and C are all constant positive numbers (L, M, P, F, C>0) and variable $V_{g8}$ also has a positive value ($V_{g8}$>0). Therefore, the circumference of the function R=f($V_{g8}$) can be a non-zero value.

The derivative of conversion rate function R with variable $V_{g8}$ is:

$$(F \times P \times M - C \times L \times M)/(P \times M + C \times V_{g8})^2$$

Considering that (F*P≠C*L) in the design of gears, under predefined conditions, the above derivative may have a non-zero value which shows that the function is either descending or ascending and does not have a maximum point or a minimum point.

The second derivative of the above function is:

$$-2 \times C \times M \times (F \times P - C \times L)/(P \times M + C \times V_{g8})^3$$

Again considering the predefined conditions, the value of the second derivative is non-zero and the function does not have a turning point. Therefore, in a defined interval, the function R is a continuous function. For example, function R can be calculated for a GCVT gearbox with following parameters.

$G_{12}=51$ $G_{13}=87$ $G_{22}=24$ $G_{23}=84$ $G_{18}=70$ $G_{19}=G_{20}=46$ $G_{26}=105$ $G_{29}=11$ $G_5=14$ $G_{17}=G_{27}=G_{28}=G_{18}=G_4=100$ $G_6=67$ $V_{g7}=10$ $V_{g8}=0.5 \ldots 10$ $A = G_{17} \times G_{28}/(G_{27} \times G_{18}) = 1$ $B = G_{16} \times G_{29}/(G_{19} \times G_{26}) = 0.15942$ $M = G_{15} \times G_{20} \times G_{18} \times G_5 \times V_{g7}/(G_{19} \times G_6 \times G_{17} \times G_4) = 1.462686$ $L = A \times G_{12} \times (G_{22}+G_{23}) = 5508$ $F = B \times G_{23} \times G_{12} = 682.955$ $P = G_{22} \times (G_{12}+G_{13}) = 3312$ $C = G_{22} \times G_{13} = 2088$

F×P≠C×L  682.955×3312≠2088× 5508→2261946.96≠11500704

$R = (L \times M + F \times V_{g8})/(P \times M + C \times V_{g8})$ $R = (5508 \times 1.462686 \rightarrow 682.955 \times V_{g8})/(3312 \times 1.462666 + 2088 \times V_{g8})$ $R = (8056.474 + 682.955 \times V_{g8})/(4844.416 + 2088 \times V_{g8})$ $V_{g8}=0.5$  R=1.426182

$V_{g8}=10$  R=0.578674.

The curve shown in FIG. 10 displays variations of value of function R based on the values of variable $V_{g8}$ between 0.5 and 1 (0.5≤$V_{g8}$≤1).

The separation of various system components in the examples described above should not be understood as requiring such separation in all examples, and it should be understood that the described components and systems can generally be integrated together in a single packaged into multiple systems.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations for the purpose of streamlining the disclosure. This method of disclosure is not to be interpreted as reflecting an intention that the claimed implementations require more features than are expressly recited in each claim. Rather, as the following claims reflect, inventive subject matter lies in less than all features of a single disclosed implementation. Thus the following claims are hereby incorporated into the Detailed Description, with each claim standing on its own as a separately claimed subject matter.

What is claimed is:

1. A transmission, comprising:
   a first shaft, extending along a first shaft longitudinal axis, the first shaft being supported by a first bearing and rotatable about the first shaft longitudinal axis;
   a first sun gear, fixed to and rotatable with the first shaft;
   a first ring gear, aligned with and rotatable about the first shaft, and including inner teeth that surround and are spaced radially from the first sun gear;
   a first planetary carrier, aligned with and rotatable about the first shaft;
   a first pinion gear, supported by the first planetary carrier and positioned between, and concurrently engaged with, the first sun gear and the inner teeth of the first ring gear;
   a second shaft, extending along a second shaft longitudinal axis, and supported by a second bearing and rotatable about the second shaft longitudinal axis;
   a second sun gear, fixed to and rotatable with the second shaft;
   a second ring gear, aligned with and rotatable about the second shaft, the second ring gear including inner teeth that surround and are spaced radially from the second sun gear;
   a second planetary carrier, aligned with and rotatable about the shaft;
   a second pinion gear, supported by the second planetary carrier, and positioned between and concurrently engaged with the second sun gear and the inner teeth of the second ring gear;
   a first interface shaft and gear assembly, supported by and rotatable within first interface shaft bearings, coupled to and rotatable by the first ring gear, and coupled to the second ring rear in a configuration wherein a rotation of the first interface shaft and gear assembly rotates the second ring gear;
   a hydraulic pump, mechanically coupled to and driven by the first interface shaft and gear assembly, and configured to output a hydraulic fluid at a volume flow rate corresponding a rotational speed of the first interface shaft and gear assembly;
   a hydraulic motor, configured to receive through a hydraulic conduit the hydraulic fluid output of the hydraulic pump, and to rotate at a rate proportional to the volume flow rate; and
   a second interface shaft and gear assembly, supported by and rotatable within second interface shaft bearings, and coupled to the hydraulic motor and to the first planetary carrier and to the second planetary carrier, and configured to transfer a rotation of the hydraulic motor to a rotation of the first planetary carrier and to a rotation of the second planetary carrier.

2. The transmission of claim 1, wherein the second interface shaft and gear assembly is configured to
   transfer a rotation of the hydraulic motor to a rotation of the first planetary carrier, according to a first ratio, and
   transfer a rotation of the hydraulic motor to a rotation of the second planetary carrier, according to a second ratio.

3. The transmission of claim 2, wherein the hydraulic pump is configured with a variable ratio of the volume flow rate to a rotational speed of the first interface shaft and gear assembly.

4. The transmission of claim 2, further comprising:
   a first planetary carrier drive gear, attached to and rotatable with the first planetary carrier; and
   a second planetary carrier drive gear, attached to and rotatable with the second planetary carrier, wherein:
   the second interface shaft and gear assembly includes:
      a second interface shaft, extending through the second interface shaft bearings,
      a second interface first gear, attached to and rotatable with the second interface shaft, and coupled to the first planetary carrier drive gear; and
      a second interface second gear, attached to and rotatable with the second interface shaft, and coupled to the second planetary carrier drive gear.

5. The transmission of claim 4, wherein:
   the first planetary carrier drive gear is configured with a first planetary carrier drive gear tooth count,
   the second planetary carrier drive gear is configured with a second planetary carrier drive gear tooth count,
   the second interface first gear is configured with a second interface first gear tooth count, wherein a ratio of the second interface first gear tooth count to the first planetary carrier drive gear tooth count is according to the first ratio, and the second interface second gear is configured with a second interface second gear tooth count, wherein a ratio of the second interface second gear tooth count to the second planetary carrier drive gear tooth count is according to the second ratio.

6. The transmission of claim 5, wherein the first interface shaft and gear assembly is configured to transfer a rotation of the first ring rear to a transfer of the second ring gear according to a third ratio.

7. The transmission of claim 6, further comprising:
a first gear attached to and rotatable with the first ring gear;
a second gear attached to and rotatable with the second ring gear, wherein:
the first interface shaft and gear assembly includes:
a first interface shaft, extending through the first interface shaft bearings,
a first interface first gear, attached to and rotatable with the first interface shaft, and coupled to the first gear; and
a first interface second gear, attached to and rotatable with the first interface shaft, and coupled to the second gear.

8. The transmission of claim 6, wherein
the first gear has a first gear tooth count,
the second gear has a second gear tooth count,
the first interface shaft first gear has a first interface shaft first gear tooth count,
the first interface shaft second gear has a first interface shaft second gear tooth count, and
the third ratio corresponds to a ratio of the first gear tooth count to the first interface shaft first gear tooth count, multiplied by a ratio of the first interface shaft second gear tooth count to the second gear tooth count.

9. The transmission of claim 1, wherein the first shaft longitudinal axis is aligned with the second shaft longitudinal axis.

10. A transmission, comprising:
a first shaft, extending along a first shaft longitudinal axis, the first shaft being supported by a first bearing and rotatable about the first shaft longitudinal axis;
a first set of solar gears, including
a first sun gear, fixed to and rotatable with the first shaft,
a first ring gear, aligned with and rotatable about the first shaft, the first ring gear including inner teeth that surround and are spaced radially from the first sun gear,
a first planetary carrier, aligned with and rotatable about the first shaft,
a first pinion gear, supported by the first planetary carrier, the first pinion gear being positioned between and concurrently engaged with the first sun gear and the inner teeth of the first ring gear;
a second shaft, extending along a second shaft longitudinal axis, the second shaft being supported by a second bearing and rotatable about the second shaft longitudinal axis;
a second set of solar gears, including
a second sun gear, fixed to and rotatable with the second shaft,
a second ring gear, aligned with and rotatable about the second shaft, the second ring gear including inner teeth that surround and are spaced radially from the second sun gear,
a second planetary carrier, aligned with and rotatable about the shaft,
a second pinion gear, supported by the second planetary carrier, the second pinion gear being positioned between and concurrently engaged with the second sun gear and the inner teeth of the second ring gear;
means for limiting a rotational speed of the first ring gear to being a first fixed ratio of a rotational speed of the second ring gear; and
means for transferring a rotation of the first ring gear to a rotation of the first planetary carrier according to a third ratio, and to a rotation of the second planetary carrier according to a fourth ratio.

11. The transmission according to claim 10 wherein means for transferring a rotation of the first ring gear to a rotation of the first planetary carrier according to a third ratio, and to a rotation of the second planetary carrier according to a fourth ratio included means for a continuous varying of the third ratio and the fourth ratio.

12. The transmission of claim 10, wherein the means for transferring a rotation of the first ring gear to a rotation of the first planetary carrier according to a third ratio, and to a rotation of the second planetary carrier according to a fourth ratio included means for selectively releasing the transferring.

* * * * *